(12) United States Patent
Xu et al.

(10) Patent No.: US 8,243,875 B2
(45) Date of Patent: Aug. 14, 2012

(54) METHOD AND DEVICE FOR IMAGING TOMOGRAPHY

(75) Inventors: Yuan Xu, Eugene, OR (US); Oleg Tischenko, München (DE); Christoph Hoeschen, Hebertshausen (DE)

(73) Assignees: State of Oregon Acting by and through the State Board of Higher Education, Eugene, OR (US); Helmholtz Zentrum Munchen Deutsches Forschungszentrum fur Gesundheit und Umwelt (GmbH), Neuherberg (DE)

( * ) Notice: Subject to any disclaimer, the term of this patent is extended or adjusted under 35 U.S.C. 154(b) by 382 days.

(21) Appl. No.: 11/920,941

(22) PCT Filed: May 19, 2006

(86) PCT No.: PCT/EP2006/004781
§ 371 (c)(1),
(2), (4) Date: Aug. 28, 2009

(87) PCT Pub. No.: WO2006/125570
PCT Pub. Date: Nov. 30, 2006

(65) Prior Publication Data
US 2009/0316856 A1 Dec. 24, 2009

(30) Foreign Application Priority Data
May 23, 2005 (EP) .................................... 05011135

(51) Int. Cl.
*G01K 23/00* (2006.01)
(52) U.S. Cl. .............................................. 378/16; 378/4
(58) Field of Classification Search ................ 378/4–20, 378/145, 147, 148, 149
See application file for complete search history.

(56) References Cited

U.S. PATENT DOCUMENTS

| 4,304,999 | A | * | 12/1981 | Richey et al. ..................... 378/4 |
| 5,608,776 | A | * | 3/1997 | Hsieh ............................. 378/145 |
| 6,094,469 | A | | 7/2000 | Dobbs et al. |
| 6,343,110 | B1 | | 1/2002 | Li |
| 2003/0053597 | A1 | | 3/2003 | Flohr et al. |
| 2004/0234021 | A1 | | 11/2004 | Hoffman |
| 2005/0089146 | A1 | | 4/2005 | Toth et al. |

FOREIGN PATENT DOCUMENTS
EP 1677253 A1 7/2006
(Continued)

OTHER PUBLICATIONS

T. Bortfeld et al., "Fast and exact 2D image reconstruction by means of Chebyshev decomposition and backprojection," Phys. Med. Biol. 44:1105-1120 (1999).
K. Hanson et al., "Local basis-function approach to computed tomography," Appl. Opt. 24:4028-4039 (Dec. 1, 1985).
(Continued)

*Primary Examiner* — Hoon Song
(74) *Attorney, Agent, or Firm* — Klarquist Sparkman, LLP

(57) ABSTRACT

An imaging method for imaging a region of investigation of an object, comprises the step of irradiating the region of investigation with at least one energy input beam along a plurality of projection directions, wherein the at least one energy input beam comprises a plurality of individual energy input beam components, wherein the energy input beam is shaped such that at least two of the energy input beam components have different cross-sections and groups of parallel energy input beam components being parallel to one of the projection directions provide a continuous irradiation of the region of investigation. Furthermore, a device for imaging the object is described.

29 Claims, 6 Drawing Sheets

FOREIGN PATENT DOCUMENTS

| | | |
|---|---|---|
| JP | 04288147 A | 10/1992 |
| JP | 2001145623 A | 5/2001 |
| JP | 2002136510 A | 5/2002 |
| JP | 2002177255 A | 6/2002 |
| JP | 2005003624 A | 1/2005 |
| WO | 1992/00566 | 1/1992 |
| WO | 2005/006986 A | 1/2005 |

OTHER PUBLICATIONS

English Translation of Notice of Reasons for Rejection for related Japanese Patent Application No. 2008-512741, mailed Feb. 14, 2012, 3 pages.

English Translation of Text of the Third Office action for related Chinese Patent Application No. 200680026890.7, mailed Mar. 9, 2012, 2 pages.

\* cited by examiner

METHOD AND DEVICE FOR IMAGING TOMOGRAPHY

STATEMENT REGARDING FEDERALLY SPONSORED RESEARCH

This invention was made with U.S. Government support under Grant DMS-020 1669 awarded by the National Science Foundation. The Government has certain rights in this invention.

CROSS REFERENCE TO RELATED APPLICATIONS

This is the U.S. National Stage of International Application No. PCT/EP2006/004781 filed May 19, 2006, which was published in English under PCT Article 21(2), which in turn claims the benefit of European Applications No. 05011135.0, filed May 23, 2005. Both applications are incorporated herein in their entirety.

TECHNICAL FIELD

The present invention relates to a method for imaging an object being irradiated with at least one energy input beam along a plurality of projection directions, in particular to a method for imaging an object on the basis of reconstructing an image function from Radon data comprising a plurality of projection functions measured corresponding to the plurality of projection directions. Furthermore, the present invention relates to a device for imaging an object on the basis of the imaging method.

TECHNICAL BACKGROUND

The non-destructive investigation of samples is an important task in various technical fields like material sciences, medical examinations, archaeology, construction technique, techniques concerning security matters etc. One approach for obtaining an image of a sample e.g. by computer tomography (CT) is based on an irradiation trough an object plane from different projection directions with X-rays, followed by a reconstruction of the object plane on the basis of attenuation data measured at different directions. The entirety of the measured attenuation data can be described in terms of so-called Radon data in a Radon space.

The most relevant conventional reconstruction methods known today can be summarized as methods based on the iterative reconstruction or those based on the so-called filtered back-projection. The iterative reconstruction methods have essential disadvantages in terms of extremely long calculation times. On the other hand, the filtered back-projection method, which relies on the so-called Fourier-slice theorem, has a general disadvantage due to an interpolation step in the reconstruction, which results in errors and artifacts that have a tendency to increase with increasing space frequency. Another problem of the filtered back-projection method is related to the discretization of the Radon data from which the image data have to be reconstructed. To get an optimal filtered back-projection reconstruction it would be necessary to exactly match the projected irradiation rays with detector elements of a detector. This is in general not the case. For this reason, uncertainties or smoothing effects from the reconstruction of Radon data by means of filtered back-projection algorithms are introduced.

T. Bortfeld et al. have described an algorithm for the reconstruction of two-dimensional images from a plurality of projections along the projection directions ("Phys. Med. Biol.", Vol. 44, 1999, p. 1105-1120). With this algorithm, the projections are represented as decompositions, which are subjected to the above filtered back-projection reconstruction. The projections are measured e.g. with a fan beam geometry, wherein attenuation values according to distinct projection lines with even angular intervals relative to each other are measured. The single projection lines measured with different projection directions of the fan beam can be resorted for providing parallel projections to be used for the image reconstruction. The algorithm of T. Bortfeld et al. has not yielded a practical implementation. The algorithm assumes an ideal fan beam geometry, which is not available in practice. Therefore, the T. Bortfeld et al. algorithm requires an interpolation step like the conventional filtered back-projection. Furthermore, the T. Bortfeld et al. algorithm has an essential disadvantage in terms of artifacts occurring in the reconstructed images.

The disadvantages of the filtered back-projection procedures and the method of T. Bortfeld et al. can be avoided with an image reconstruction method, which is described in the non-published European patent application EP 04031043.5. With this method, the image function is determined from Radon data comprising a plurality of projection functions measured corresponding to the plurality of predetermined projection directions. The image function is determined as a sum of polynomials multiplied with values of the projection functions. In practical implementations, this image reconstruction is based on the measurement of attenuation values corresponding to discrete irradiation beam components having equal angles relative to each other. According to non-published EP 04031043.5, the discrete beam components can be generated with a fan beam geometry by using a radiation source 210' equipped with a source mask 211' as schematically illustrated in FIG. 12. The source mask 211' comprises a shielding plate 212' for example made by tungsten with through holes 213'. The shielding plate 212' of the source mask 211' can have a planar shape as shown in FIG. 12 or a cylindrical shape. The through holes 213' are arranged such that projection lines starting at the radiation source cross a circle with detector elements with an equal arc length spacing.

In contrast to the T. Bortfeld et al. algorithm, the image reconstruction of unpublished EP 04031043.5 can be used to replace the conventional filtered back-projection algorithm. Therefore, the artifacts introduced by the interpolation in filtered back-projection could be avoided. Nevertheless, it has been found that the image reconstruction according to EP 04031043.5 in practice may have disadvantages in terms of artifacts in the reconstructed image (so-called aliasing artifacts).

Current developments in computed tomography have provided so-called multi-slice-CT and CT-systems based on flat panel technology. These developments are suffering from three further major problems. First of all, the amount of data is very large, the reconstruction time for such an amount of data is too long or the computers needed to handle such data are too expensive. The second problem results from the planar geometry of the detector, which generally is not adapted to the circle geometry of conventional CT devices. Finally, resolution of low contrast details is restricted due to scattered radiation.

The above disadvantages are associated not only with the conventional CT imaging, but also with all available reconstruction methods related to Radon data.

OBJECTIVE OF THE INVENTION

The objective of the invention is to provide improved methods for imaging an object, which avoid the disadvantages of the above conventional techniques and which in particular are capable of reducing artifacts in image reconstruction. Furthermore, the imaging method is to be improved so that it can use an application of flat panel detectors. Furthermore, the objective of the invention is to provide an improved imaging device, which is capable of improved imaging a region of investigation in particular with reduced aliasing artifacts.

The above objectives are achieved with methods or devices comprising the features of patent claims 1 and 19. Advantageous embodiments and applications of the invention are defined in the dependent claims.

SUMMARY OF THE INVENTION

According to a first general aspect of the invention, an energy input beam for irradiating a region of investigation is provided with a plurality of individual, discrete energy in-put beam components at least two of which having different cross-sections. The energy input beam components are travelling through the region of investigation. Groups of parallel energy input beam components belonging to one or different energy input beams provide a step-less irradiation through the region of investigation. The energy input beam is formed such that the parallel energy input beam components are arranged with an abutting fashion so that the region of investigation is completely covered with the irradiation according to the respective projection direction.

The inventors have found that artifacts (in particular aliasing artifacts) can be generated by the conventional techniques. If the projection lines are spaced from each other with equal angles as required, the corresponding energy beam components intersect a reference plane perpendicular to the current projection direction of the energy beam at non-equidistant intersection points. Accordingly, the image reconstruction algorithm described in unpublished EP 04031043.5 and the conventional algorithm of T. Bortfeld et al. are characterized by a non-uniform sampling. With the conventional energy beam components having equal cross-sections, this non-uniform sampling yields in most cases either an overlap or gaps between neighboring parallel energy beam components. The inventors have found that these overlaps or gaps are responsible for the aliasing artifacts obtained with the conventional imaging methods.

Contrary to the above techniques with non-uniform sampling, the imaging method of the invention provides for a continuous irradiation of the region of investigation. As the energy beam components being parallel to a current projection direction have different cross-sections, the non-uniform sampling can be compensated. Accordingly, the parallel energy beam components are abutting relative to each other. Any double irradiation or unintended shadowing is avoided so that the aliasing artifacts are suppressed.

The energy input beam shaping according to the invention has a further important advantage with regard to the design of the detector device for measuring attenuation values obtained with the irradiation of the region of investigation. For providing the continuous irradiation of the region of investigation, the cross-sections of energy beam components are decreasing with increasing distance from a central energy input beam component. The larger an angle between a particular energy input beam component and the central energy input beam component is, the smaller is the cross-section of the particular energy input beam component. This cross-section reduction from the center towards the boundaries of a group of parallel energy input beam components even yields equal cross-sections of the projections of the energy input beam components on a straight, linear (1-dimensional) or a planar (2-dimensional) detector device oriented perpendicular to the projection direction of the considered group of energy input beam components. As a result, each energy input beam component is sensed with the same number of detector elements of the detector device so that a further calibration or resizing of groups of the detector elements can be avoided.

While the conventional computer tomography is defined as being based on irradiating the region of investigation with beams having equal cross-sections, the inventors have departed from this concept. Nevertheless, the term "computer tomography" is maintained in the following for describing embodiments of the imaging method according to the invention.

The term "region of investigation" (ROI) used herein generally refers to an object under investigation or a part thereof. The ROI can be described as a 2- or 3-dimensional entity. The term "projection direction" used herein generally refers to the linear course of an energy input through the ROI. The projection direction can be defined by angles relative to a coordinate system used. If fan or cone beams are considered, the term "projection direction" indicates the orientation of a central (or: main) beam component in the fan or cone beam.

Radon data measured at the ROI are obtained from a set of projection functions which have been determined corresponding to a plurality of predetermined projection directions running through the ROI. The data are collected with a certain number of "projections". These projections are characterized by integrating the interesting effect along strips covered by the beam components. By measuring a sufficient number of these integrated "projections", the features of the object can be reconstructed from the Radon data.

The values of the projection functions generally are determined by the interaction (in particular attenuation, e.g. by absorption, scattering or reflection) of an energy input beam travelling through the ROI along the respective projection direction. While the projection function is a one-dimensional function, the entirety of projection functions corresponding to all available projection directions spans a space (Radon space) of higher dimensions.

The term "energy input beam" (or: "radiation beam") used herein refers to all types of a physical quantity, which travels along a straight line (or an essentially straight line) through the ROI while the energy carried is changed due to an interaction with the ROI. In particular, the term "energy input beam" covers electromagnetic radiation, in particular X-rays, particle radiation or sound waves.

According to a preferred embodiment of the invention, the energy input beam components, which belong to different energy input beams or to one particular energy input beam, provide groups of parallel energy input beam components irradiating the ROI without gaps and without overlap between neighboring energy input beam components. The essential advantage of this embodiment of the invention is given by the fact that the aliasing artifacts can be suppressed in a particular efficient manner. In practice, the boundaries of the energy input beam components are not jumps in a function, but rather a continuous function depending on the particular beam shaping technique. Therefore, the feature of gap-free and overlap-free irradiation (or: complete irradiation) is fulfilled, if the physical quantity (e.g. electromagnetic field strength) between two energy beam components is not higher than 50% compared with the respective physical quantity in the center of the adjacent energy beam components.

The present invention represents a further important advantage as the energy input beam shaping can be implemented with conventional imaging techniques, e.g. conventional computer tomography imaging techniques. Therefore, the energy input beam shaped according to the invention preferably is a fan beam or a cone beam created with at least one beam source and having a particular beam angle describing the divergence of the fan or cone beam.

If the energy input beam is shaped with a beam mask, particular advantages can be obtained with regard to a precise and reproducible input method that provide the energy input beam components within a predetermined beam angle and with predetermined cross-sections. The beam mask includes through holes, which transmit the energy input beam components while remaining parts of the energy input beam are shielded. The beam mask can be arranged near a beam source and may even move as a source mask with the beam source, e.g. an X-ray source. In this case, the beam mask is called source mask. Otherwise, a beam mask fixed to at the imaging device is called frame mask. Due to the geometrical size of beam sources typically used for Radon data based imaging methods, the beam mask allows a sharp profiling of the energy input beam. The inventors have found that the continuous irradiation of the ROI can be provided even at a distance from the beam source (combined with the beam mask) up to the range of 1 meter or more.

According to a preferred embodiment of the invention, the beam mask (as a movable source mask or as a fixed frame mask) comprises a planar solid plate made of a shielding material including the through holes. The solid plate is arranged with a distance s from the X-ray emitter. The through holes all have an equal size. They are arranged at positions $s_j = s \cot \theta_j$ (with $\theta_j$ describing the orientation of the individual beam components). With the planar beam mask arranged perpendicular to the central projection direction of a fan or cone beam, the through holes with equal sizes automatically provide energy input beam components with decreasing cross-section at the boundaries of the energy input beam. The planar beam mask has particular advantages in terms of a simple construction and broad application range. Alternatively, the beam mask may be formed by a curved, e.g. a cylindrical member of shielding material including the through holes. In this case, the through holes have different sizes for providing the different cross-sections of the energy input beam components. The cylindrical beam mask has particular advantages with regard to a precise definition of the cross-sections independently on the adjustment relative to the beam source.

The curved geometry of the beam mask and the diameters of the through holes can be modified such that any projection of beam components on a plane perpendicular to the current projection direction have the same size.

If the imaging method of the invention includes an adjustment of the beam mask relative to the energy input beam source, the imaging and reconstruction results can be improved by a fine adjustment of the beam mask.

According to a further advantageous embodiment of the invention, the energy input beam is shaped not only with regard to the profiling of the energy input beam components, but also with regard to the outer boundary of the energy input beam. To this end, the imaging method of the invention comprises a further step of setting the beam angle of the energy input beam. This embodiment has particular advantages with regard to an adaptation of the beam source (possibly in combination with the beam mask) to a particular object to be investigated. For irradiating a small object, the beam angle can be decreased so that the overall irradiation dose can be reduced.

Preferably, the beam angle is set with an aperture serving as a diaphragm or shutter. Advantageously, the aperture has a simple construction. Furthermore, it can be simply mounted on a conventional imaging device, like e.g. a conventional CT device for an adaptation to the present invention. Further advantages of the aperture arise from the availability of two degrees of freedom for adjusting the beam angle. With a first alternative, the beam angle is adjusted by setting a diameter of the aperture. This allows a flexible adaptation of the aperture to the object under investigation. According to a second alternative, the beam angle is adjusted by setting a distance between the aperture and the beam source. With the decreasing distance, the beam angle is increased. Both alternatives can be combined.

According to a second preferred embodiment of the invention the at least one energy input beam comprises a distribution of parallel pencil beams providing the energy input beam components. In this case, each group of parallel energy input beam components belongs to one energy input beam only. This energy input beam is created with a linear beam source as it is known e.g. in conventional CT imaging devices.

Shaping the energy input beam for providing the at least two pencil beams with different cross-sections is obtained by modulating the output of the linear beam source or by a beam mask with adapted geometry.

The above reconstruction algorithms based on discrete projection lines inquire the measurement of attenuation values according to projection lines intersecting a reference plane perpendicular to the actual projection direction at non-equidistant intersection points. Therefore, the above consideration concerning the effect of energy beam components with equal cross-sections is valid for parallel pencil beams as well. With this embodiment of the invention, the parallel pencil beams represent the energy input beam components of a particular energy input beam. While it is possible to adjust the cross-sections of the pencil beams with a beam mask as outlined above, preferably, the different cross-sections of the parallel pencil beams are adjusted by modulating the beam source output.

With an X-ray beam source, the parallel pencil beams are preferably created subsequently with a moving beam source emitter. In this case, the electron current for generating the X-rays is modulated for adjusting the cross-section of the pencil beams.

For taking a complete set of Radon data of the object under investigation, the ROI has to be irradiated along a plurality of projection directions. This irradiation can be obtained with a plurality of energy input beams created with a plurality of beam sources. With this embodiment, beam sources are distributed around the object to be imaged. However, according to a preferred embodiment of the invention, the projection directions are set subsequently by moving the energy beam source relative to the object. Preferably, the energy beam source is moved on a circle around the object. Advantageously, this embodiment is completely compatible with conventional imaging techniques, in particular with conventional computer tomography.

The imaging method of the invention can be implemented with any type of detector that is capable of measuring attenuation values of the energy beam transmitted through the ROI. If according to a preferred embodiment of the invention, at least one straight or planar detector is used for measuring the attenuation values, particular advantages arise in terms of compatibility with conventional detection techniques and availability of detectors with simple (planar) geometry. Furthermore, if the energy input beam comprises a group of parallel pencil beams, the attenuation values of all pencil beams can be measured simultaneously with one detector only. With fan beams or cone beams, a plurality of detectors or one detector only can be used. In the latter case, the detector is moveable corresponding to the moving energy beam source.

The present invention provides another essential advantage in terms of data handling. Due to the adjustment of the cross-sections of the energy input beam components, attenuation values can be measured with predetermined groups of detector elements of the detector device. The groups of detector elements have equal sizes for all beam components. Only these predetermined groups are to be read out without resizing so that the amount of data to be processed is reduced.

For completing the image reconstruction, the imaging method of the invention preferably comprises a step of subjecting the measured attenuation values to an image reconstruction procedure. For compensating the dose reduction effect of the inclined projections, the attenuation values are scaled by dividing them by the ray thickness of the beam components contributing to the respective attenuation values. Preferably, the image reconstruction procedure comprises one of the algorithms mentioned above. EP 04031043.5 and the publication of T. Bortfeld et al. are introduced into the present specification by reference. This introduction comprises in particular the features concerning the implementation of the image reconstruction algorithms.

It is an essential advantage of the invention, that the imaging method and device can be used in various applications in medical imaging, for example CT, etc. However, there are a lot more possible applications like light tomography, any multidimensional imaging for industrial testing or biological research and so on. Preferably, the image function is determined from Radon data measured in an X-ray computer tomography (CT) device, or a neutron based transmission detection system.

According to a second general aspect of the invention, the above objective is solved by an imaging device including a measuring device, which comprises at least one energy input beam source for creating the above energy input beam with individual energy input beam components, wherein the measuring device further comprises a shaping device for adjusting the cross-sections of the energy input beam components. According to a preferred embodiment of the invention, the shaping device comprises a beam mask with through holes arranged between the energy beam source and the ROI, preferably in front of the energy beam source. Alternatively, the shaping device comprises a control device for modulated operation of the energy beam source, like e.g. a current control device for modulating the electron current of an X-ray source.

According to further preferred embodiments of the invention, the imaging device comprises at least one of a first adjustment device for adjusting a distance between the source mask and the energy input beam source and a second adjustment device for adjusting a diameter of an beam angle aperture and/or a distance between the aperture and the energy input beam source.

BRIEF DESCRIPTION OF THE DRAWINGS

Further details and advantages of the invention are described in the following with reference to the attached drawings, which show.

EMBODIMENTS OF THE INVENTION

The invention is described in the following with reference to the application in computer tomography. It is emphasized that the invention can be implemented in an analogous way with the other applications mentioned above. Furthermore, the following description of the preferred embodiments mainly refers to the step of energy beam shaping. Details of CT or other imaging devices or image reconstruction algorithms used for implementing the invention are not described as far as they are known from conventional techniques or from EP 04031043.5.

Figure 1:
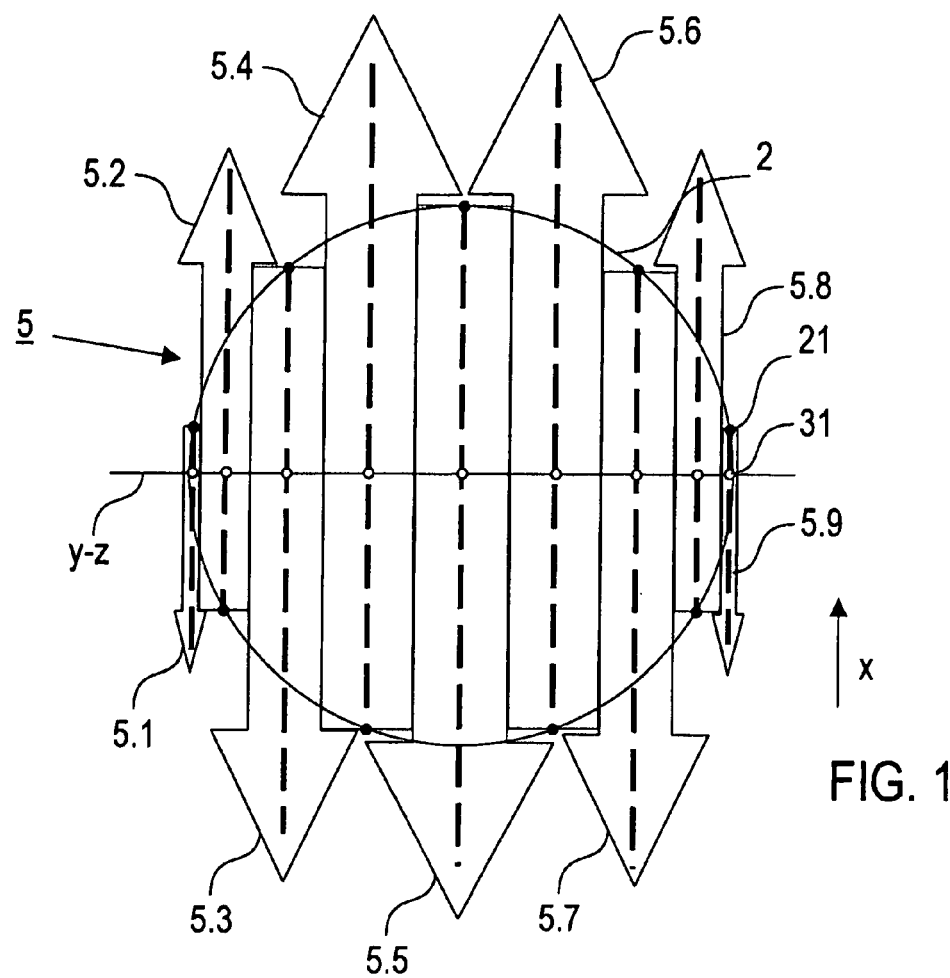
FIG. 1 a schematic illustration of an embodiment of beam shaping according to the invention.
Figure 12:
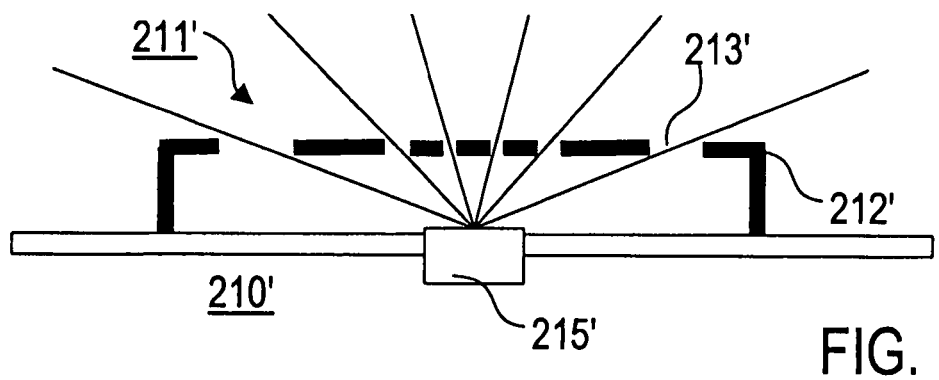
FIG. 12 a schematic illustration of a beam shaping mask according to unpublished EP 04031043.5.

Beam shaping according to the invention is schematically illustrated in FIG. 1, which shows the 2-dimensional case of imaging a plane intersecting an object. With the circle 2 representing the ROI to be reconstructed, black dots 21 on the circle 2 are positions of an X-ray source for creating radiation beams each including one of the illustrated X-ray radiation beam components (arrows). White dots 31 represent the distribution of e.g. nine discrete beam components 5.1 to 5.9 (or: projection lines), which form a group 5 of parallel energy input beam components as required for the above algorithms based on a discrete sampling. Simultaneously, the white dots 31 are virtual representations of the positions of bins of the detector device. With the real arrangement, the source and detector devices are positioned outside the ROI (see below, FIGS. 3, 12).

The above reconstruction algorithms with discrete sampling require the measurement of projection functions (see FIG. 2) comprising a plurality of attenuation values each measured according to one of the radiation beam components. A plurality of projection functions is measured along a plurality of projection directions. As an example, the projection direction "x" (see arrow) is illustrated. According to the positions of the source and detector devices arranged for providing the beam 5, the beam components 5.1 to 5.9 are illustrated with opposite directions (+x/−x). For 3-dimensional imaging in helical computer tomography, all radiation beam components can be oriented with the same direction.

The required irradiation of the ROI with equi-angle geometry of energy input beam components is associated with an intersecting of a reference plane (y-z) perpendicular to the current projection direction at non equidistant intersection points (see below, FIGS. 6, 7). After resorting energy input beam components into groups of parallel components according to a particular projection direction, these parallel components still have intersection points with the reference plane, which are not evenly distributed. This feature is shown in FIG.

1. The intersecting points (white dots 31) form decreasing intervals with increasing distance from the central beam component 5.5.

According to the invention, the cross-sections of the energy input beam components (here: X-ray beam components) are selected to have a decreasing cross-section with increasing distance from the central beam component 5.5. Furthermore, the cross-sections are selected such that the ROI is totally covered by the irradiation and the white dots 31 are in the middle of the respective beam component.

The diameter $d_j$ of one given beam component is defined by $$d_j = 2\tan\left(\frac{\pi}{2(2m+1)}\right)\sin(\theta_{j,2m})$$
$$j = 0, 1, \ldots 2m$$

or $$d_j = d\sin\theta_{j,2m}$$

wherein $\theta_{j,2m}$ corresponds to the equi-angle geometry of data collection and depends on geometry chosen and d is a measure for the resolution of imaging.

Further details of the provision of energy input beam components are illustrated below.

Figure 2:
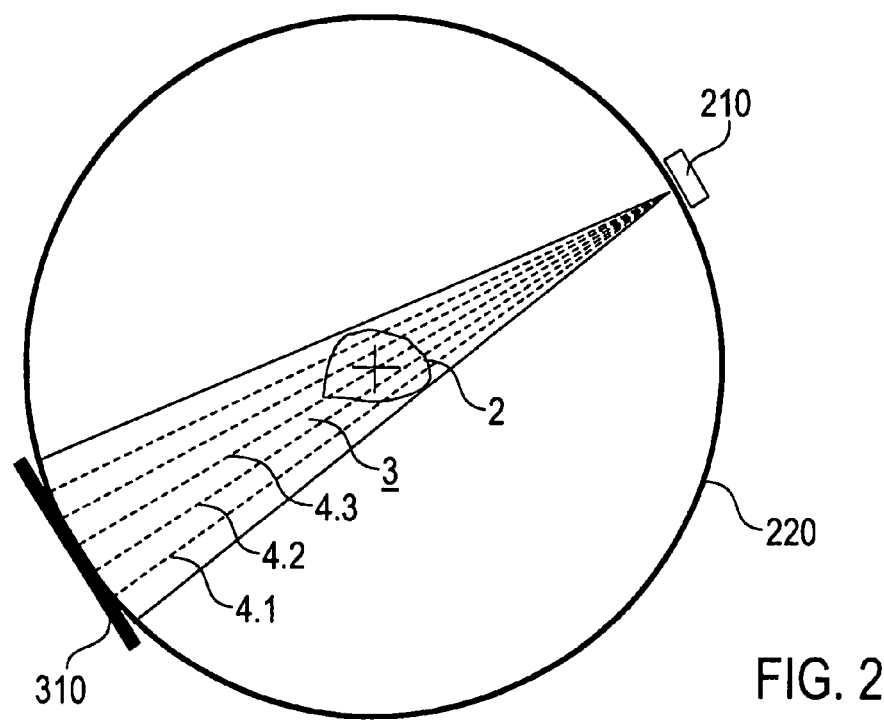
FIGS. 2 and 3 illustrations of directing fan beams through an object under investigation.

If the invention is applied in computer tomography, the imaging device is structured like a current medical CT-system. Directing a continuous fan or cone beam 3 through ROI in a CT system for collecting projection data is schematically illustrated in FIG. 2. The CT-system (not completely illustrated) includes the ring-shaped source carrier 220 in which the X-ray tube (radiation source 210) and the planar detector device 310 are rotating in a way that the whole system can finish a complete turn within e.g. 0.3 to 0.5 s. The detector device 310 consists e.g. of 1 to 64 rows (or up to 256 rows or more) of detector elements (if it is more than one row it would be called a multi-slice-CT) and approximately 700 and 1000 detector elements per row. Within each single turn the data are read according to the number of required projections, e.g. about 1000 times. The object under investigation, e.g. a patient, is moving through this CT-ring, lying on a patient table, that is moving continuously. By this method a so-called helical or spiral CT data set can be gathered, because the data that are collected are located on a spiral net. The detector device 310 is a straight (1-dimensional) or a planar (2-dimensional) arrangement of detector elements being arranged on a plane reference surface perpendicular to the projection direction from the radiation source.

Figure 3:
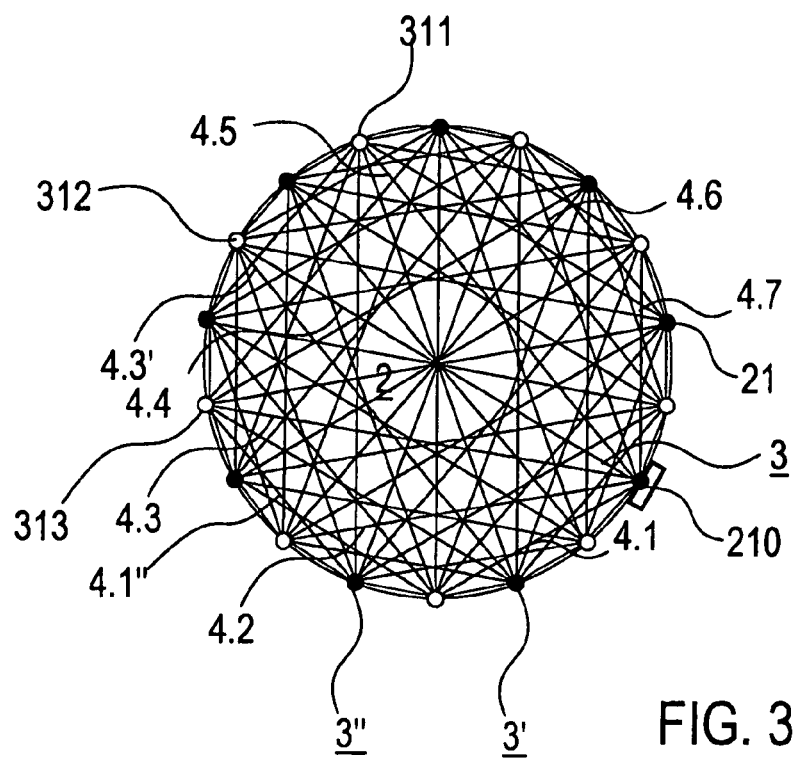

The selection of parallel beam components e.g. for a complete covering of the ROI can be done with a conventional CT-system as outlined in the following. Reference is made to fan beams, while cone beams are handled in an analogue way. Each fan beam 3 as illustrated in FIGS. 2 and 3 represents a bundle of fan beam components 4.1. 4.2, 4.3 . . . . Each of the fan beam components 4.1, 4.2, 4.3 . . . can be considered as a straight pencil beam. While these pencil beams as such do not have the same projection directions, the determination of the discrete projection profiles according each required projection direction follows a concept, which is illustrated in FIG. 3.

FIG. 3 illustrates a plurality of fan beams (e.g. fan beam 3) each of which comprising the fan beam components 4.1 to 4.7. Black dots 21 are positions of the X-ray source creating the illustrated X-ray radiation fan beams. For a first main projection direction corresponding to the illustrated position of the radiation source 210, the fan beam component 4.5 runs through ROI 2 as a straight pencil beam being detected at the detector element 311 (or a group of detector elements) of the detector device (detector array). For obtaining an attenuation value of another projection line parallel to the fan beam component 4.5, e.g. the fan beam components 4.3' or 4.1" of the fan beams 3' or 3" radiated at changed positions of the radiation source 210 are detected at the detector element 312 or 313, resp. With an appropriate selection of the detector element positions and the radiation source positions, in particular with an arrangement of these positions spaced with equal arc lengths, attenuation values measured with fan beam components having the same projection and in particular being parallel can be used for constructing the discrete projection profile. The fan beam components 4.5, 4.3' and 4.1" have different relative positions within the fan beams 3, 3' and 3". With the use of beam masks described below, the fan beam components 4.5, 4.3' and 4.1" have different cross-sections (decreasing from the centre to the boundary of the beam), so that a distribution of cross-sections as illustrated in FIG. 1 can be obtained in the group of parallel beam components.

Figure 8:
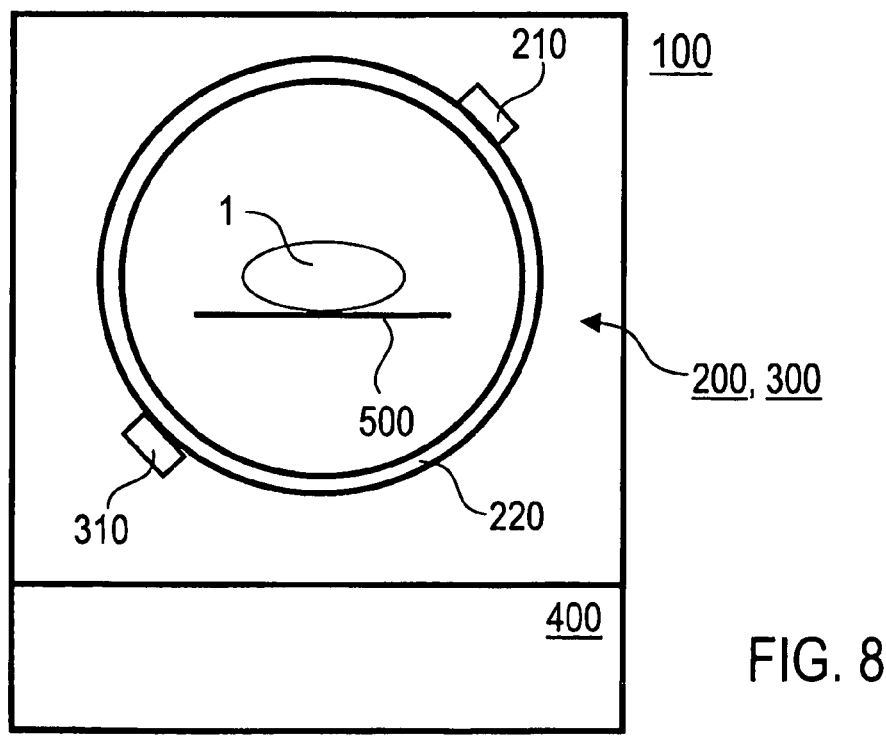
FIG. 8 a schematic representation of an embodiment of an imaging device according to the invention.

This concept can be used for the reconstruction of image functions from projection data collected with a CT device e.g. according to FIG. 8. As the positions of the radiation source 210 and the detector device and the positions of the detector elements 311, 312, 313, . . . within the detector device are known from each selected central projection direction of the fan beam, the integrated attenuation values for constructing discrete projection profiles corresponding to groups of parallel beam components can be simply obtained from the collection of raw data obtained with the CT device and resorting the sensed integrated attenuation values.

Figure 4:
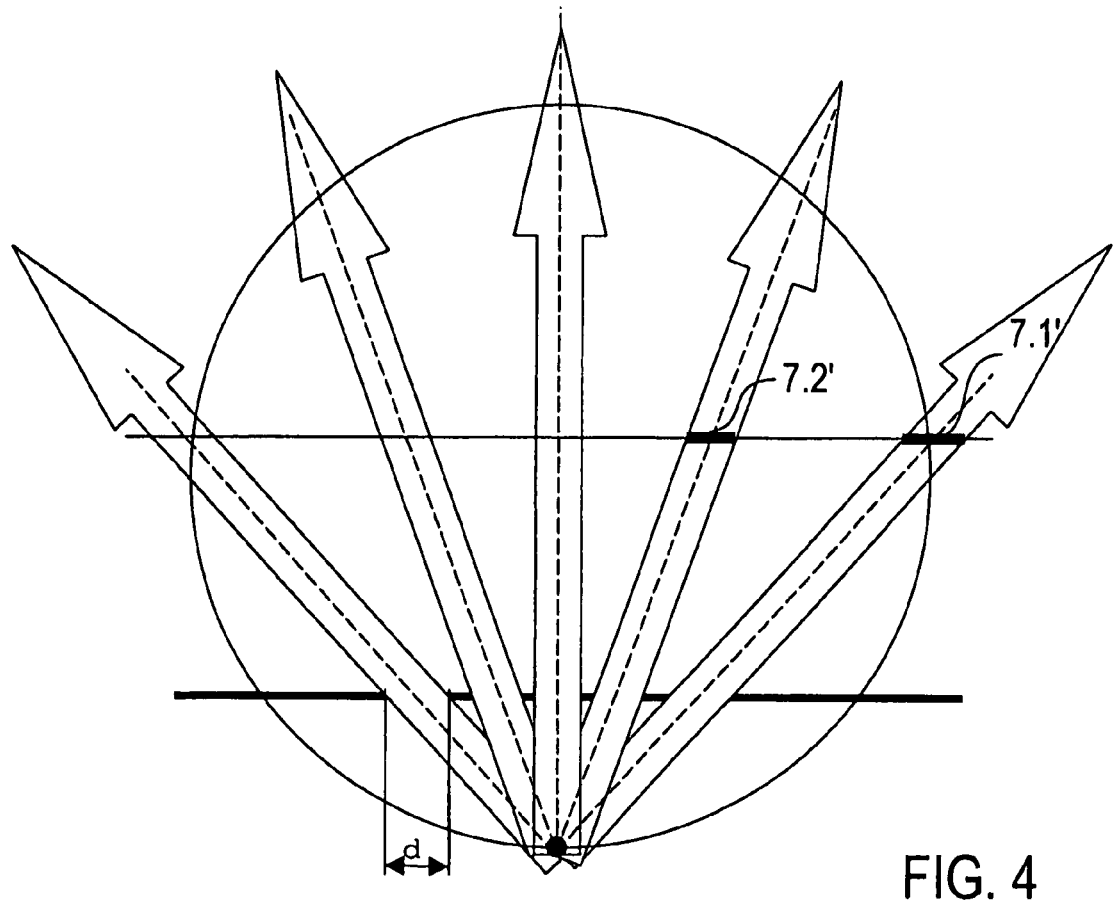
FIG. 4 an illustration of the effect of conventional irradiation with beam components having equal cross-sections.
Figure 5:
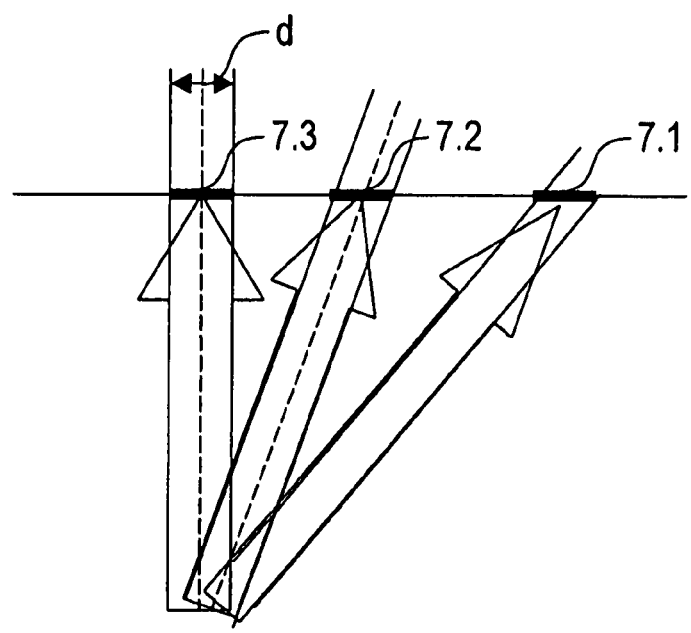
FIG. 5 a schematic illustration of the effect of irradiation with beam components having different cross-sections according to the invention.

The effect of providing shaped beam components having different cross-sections according to the invention is illustrated with further details in FIGS. 4 and 5. FIG. 4 shows the effect of a source mask according to FIG. 12 as described in EP 04031043.5. For providing beam components with equal cross-sections, this source mask has through holes with varying diameters $d_j$. With increasing distance from the central through hole, the diameters $d_j$ are increasing. As a consequence, the projections of the beam components in the detector plane are increasing, e.g. the projection 7.1' is larger than the projection 7.2'. This effect is compensated with the beam shaping according to the invention as shown in FIG. 6. All projections 7.1, 7.2 and 7.3 onto the detector plane have the same size.

Figure 6:
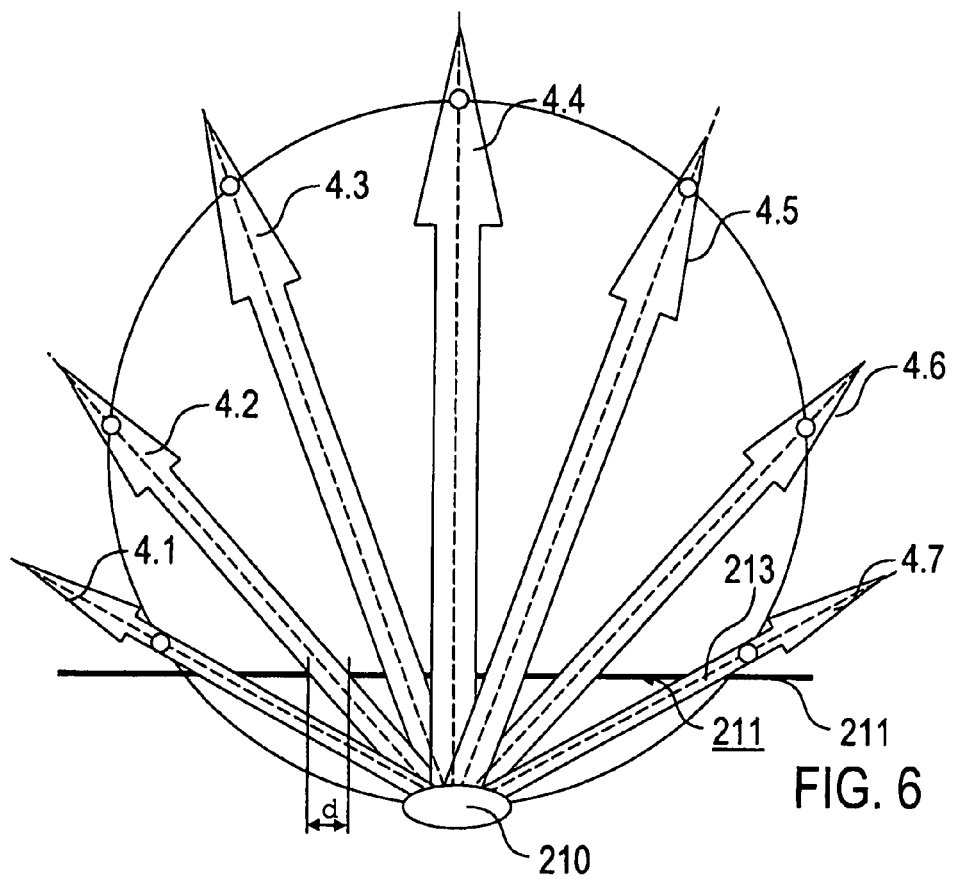
FIGS. 6 and 7 schematic illustrations of possible embodiments of beam shaping masks used according to the invention.
Figure 7:
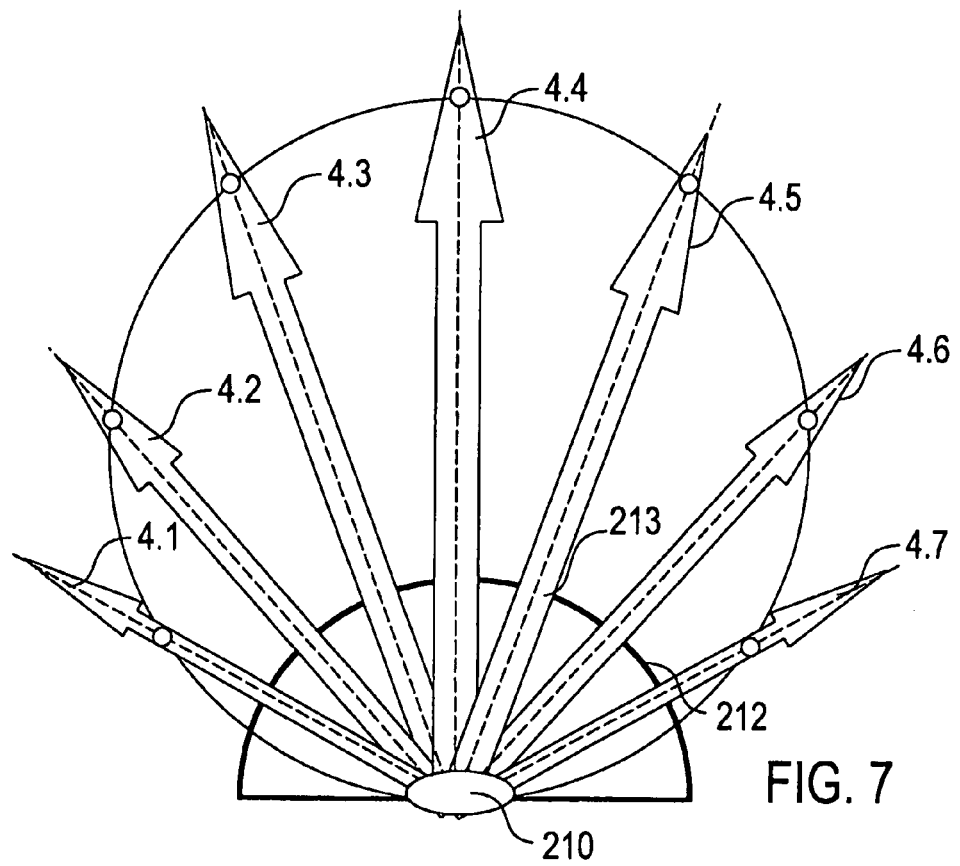

FIGS. 6 and 7 illustrate embodiments of beam shaping with beam masks 211 used according to the invention. The seven discrete beam components 4.1 to 4.7 are generated with a fan beam geometry by using a radiation source 210 equipped with the source mask 211. According to FIG. 6, the source mask 211 comprises a shielding plate 212 of e.g. tungsten with through holes 213. The through holes 213 are arranged such that the projection lines starting at the radiation source 210 cross the circle in line with the detector elements at predetermined positions, in particular, they are arranged with an equal arc length spacing. In contrast to the shielding plate 212' shown in FIG. 12, the through holes 213 in the planar plate have identical diameters d. The thickness of the shielding plate 212 is with the use of tungsten in the range of about 100 μm to about 5 mm. FIG. 6 illustrates seven beam components for clarity reasons only. In practice, the shielding plate 212 includes e.g. about 200 holes with a diameter of approximately 100 μm. The size of the holes is selected in dependence on the imaging resolution to be obtained.

The central beam component 4.4 perpendicularly intersects the mask plate and correspondingly the detector plane (not shown). Accordingly, the cross-section of the central beam component 4.4 is equal to the diameter d. On the other hand, the beam component 4.1 at the boundary is tilted relative to the mask plate. Therefore, the cross-section of the beam component 4.1 is reduced. Generally, with a numbering starting from a central through hole to the boundary (up to the m-th through hole), the cross-section of the corresponding m-th beam component is $$d = 2\tan\left(\frac{\pi}{2(2m+1)}\right)$$

According to FIG. 7, the source mask 211 comprises a (half-)cylindrical shielding member 212 of e.g. tungsten with through holes 213. The cylindrical shielding member 212 is oriented with the cylinder axis parallel to the axis of the CT ring. The through holes 213 in the cylindrical member have different diameters for exactly providing the different cross-sections of the beam components.

FIG. 8 schematically illustrates an embodiment of the imaging device 100. The imaging device 100 comprises the measuring device with an energy generator 200 and the detector device 300 and the reconstruction device 400 being connected with the measuring device. Furthermore, a holding device 500 is provided, which is e.g. a carrier table as it is known from CT systems or any other carrier or substrate holder for arranging an object 1 under investigation in the measuring device and for adjusting the geometry of the object relative to the energy generator 200 and the detector device 300. Further components like a control device, a display device etc. (not shown) are provided for as they are known per se from prior art devices.

The energy generator 200 comprises an energy input source 210, like e.g. a movable X-ray source arranged on a source carrier 220 (e.g. a guide rail or gantry) as it is known from conventional CT devices. The detector device comprises a detector array 310 which is movably arranged on the source carrier 220 opposite of the energy input source 210. With this structure, the projection direction through the ROI (parallel in the plane of drawing) can be set by rotating the combination of components 210, 310 around the holding device 500. Alternatively, a detector device with a distribution of detector arrays around the object 1 is fixed relative to the source carrier 220.

Figure 9:
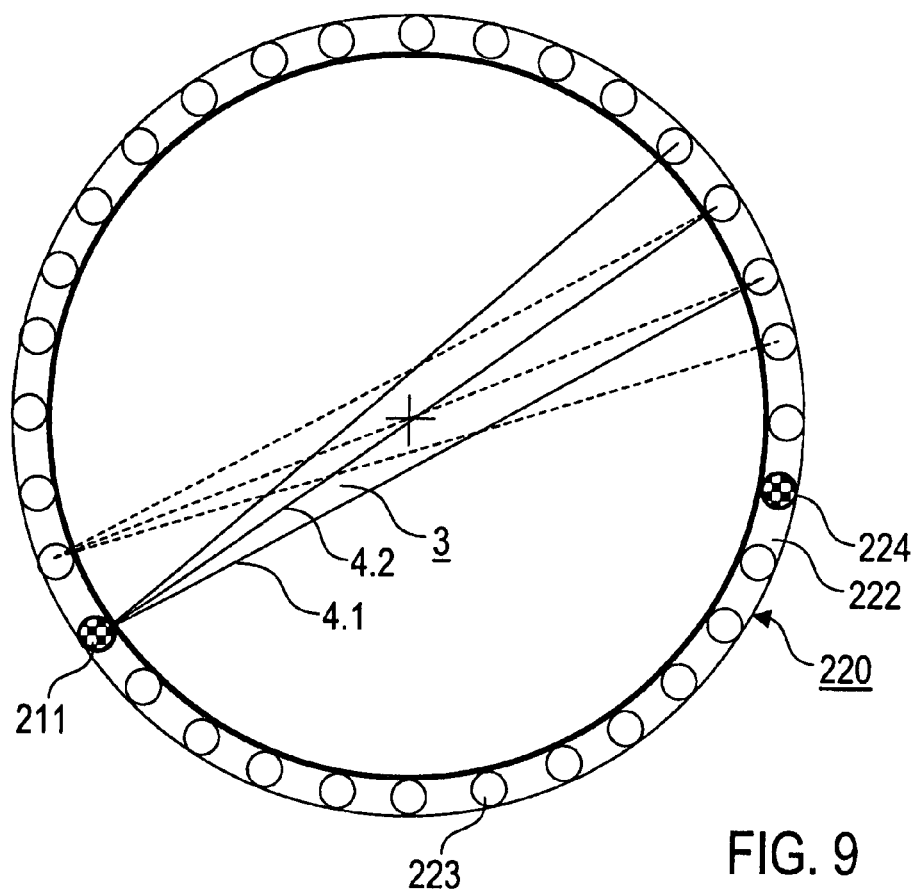
FIG. 9 a further illustration of directing fan beams through an object under investigation.

FIG. 9 shows further details of various embodiments of the source carrier 220. Firstly, the discrete fan beam 3 comprising fan beam components 4.1, 4.2, ... is generated with a radiation source combined with the source mask 211. The source mask 211 is adapted for shaping the energy distribution function of the radiation source as outlined above. The source mask is fixed to the radiation source (e.g. X-ray tube), in particular to a frame 214 of an output window 215 of the radiation source 210 by a detachable fixing element, like e.g. a clip element, a snap connection or an adjustable carrier (see FIG. 10). Secondly, the shielding function can be fulfilled by a ring-shaped shield 222 which is schematically illustrated with a plurality of radiation windows 223. The ring-shaped shield 222 can be detachably fixed to the source carrier 220 for adapting the geometric properties of the shield 222 to the practical application and in particular to the mask used. As an example, the ring-shaped shield 222 comprises 201 radiation windows 223 each having a diameter of 6 mm (with a diameter of the CT-ring: 80 cm).

The source masks 211 described above can be omitted if each radiation windows 223 of the ring-shaped shield 222 is provided with a frame mask 224 which is illustrated in FIG. 9 as one example only. In fact, the source and frame masks 211, 224 need not be provided simultaneously.

With the discrete fan beam generated by the mask illustrated above, the signals from the detector elements of the detector device detecting the integrated values of e.g. attenuation along the corresponding projection lines are read-out at certain positions of the radiation source and the detector device only. The read out positions are those arc length positions on the ring-shaped source carrier, which fulfil the condition of selecting fan beam components with the same projection directions as illustrated in FIG. 3.

Figure 10:
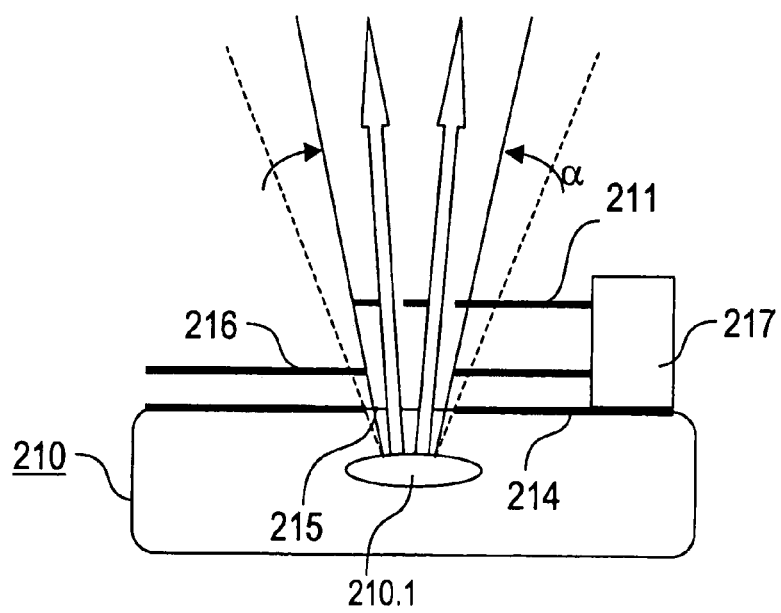
FIG. 10 a schematic illustration of the combination of a beam source with a beam angle aperture and a source mask according to the invention.
Figure 11:
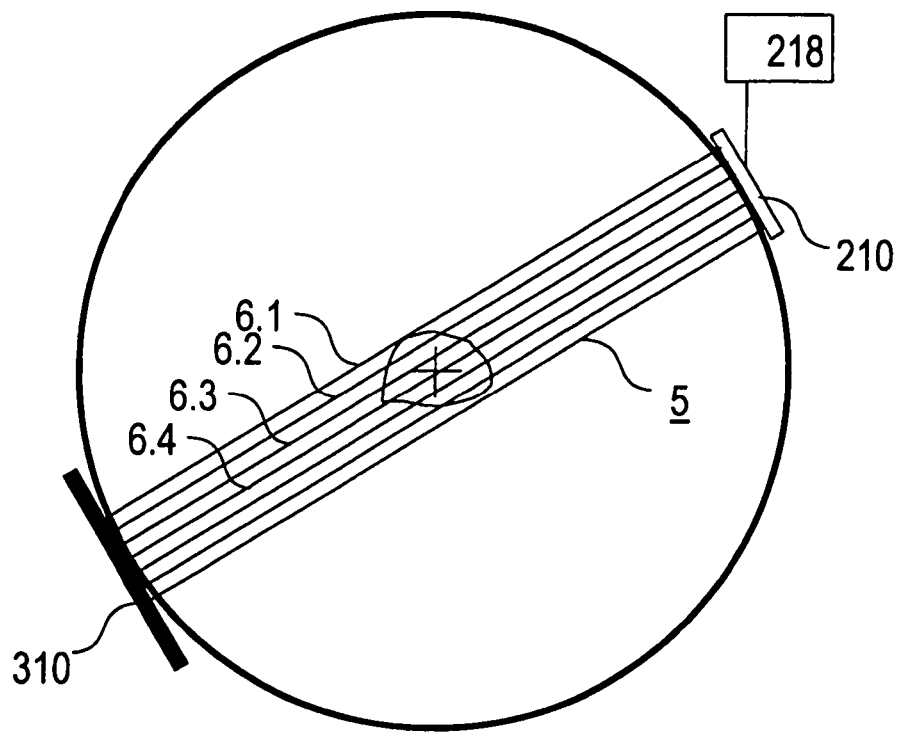
FIG. 11 a further illustration of directing pencil beams through an object under investigation.

FIG. 10 shows an embodiment of combining the radiation source 210 with the source mask 211 and a beam angle aperture 216. The adjustable carrier 217 is arranged on the frame 214 of the output window 215 for holding at least one of the components 211 and 216. Generally, the adjustable carrier 217 serves as at least one adjustment device. The beam angle aperture 216 is made of a shielding plate with a central hole. The diameter and/or the perpendicular distance between the beam angle aperture 216 and the radiation emitter 210.1 of the radiation source 210 can be adjusted with the adjustable carrier 217 for defining the beam angle a of the radiation beam 3. The source mask 211 is shaped as outlined above for defining the beam components 4.1, 4.2. The distance between the source mask 211 and the radiation emitter 210.1 can be varied for obtaining a required imaging resolution. The adjustable carrier 217 can be operated manually or electrically, e.g. with piezo-electric drive units.

According to a further embodiment to the invention, the object under investigation can be irradiated with straight, parallel pencil beams 6.1, 6.2, 6.3, ... emitted simultaneously at each position of the radiation source 210 as shown in FIG. 10. The beam 5 comprising the straight parallel pencil beams 6.1, 6.2, 6.3, ... is distributed on a radiation field, the extension of which is determined by a linear, elongated radiation source. The parallel pencil beams 6.1, 6.2, 6.3, ... are shaped with a mask provided on the radiation source as described above. Alternatively, a moving radiation source emitting one pencil beam can be used as it is known from the CT-systems of the first generation. In this case, the cross-section of the pencil beam is controlled with the current control 218 of the source 210. The embodiment of FIG. 10 has the particular advantage that discrete projection profiles can be directly measured with the detector device 310 without the resorting component selection as shown in FIG. 3.

The invention claimed is:

1. An imaging method for imaging a region of investigation of an object, comprising:
   irradiating the region of investigation with at least one energy input beam along a plurality of projection directions, wherein the at least one energy input beam comprises a plurality of individual energy input beam components and has a beam angle describing a divergence of the energy input beam; and
   shaping the energy input beam using a beam mask made of an energy input shielding material with through holes, each of which transmitting one of the energy input beam components while remaining parts of the energy input beam are shielded, such that at least two of the energy input beam components are provided for irradiating the region of investigation, wherein the at least two of the energy input beam components have different cross-sections and wherein groups of parallel energy input beam components being parallel to one of the projection directions provide a continuous irradiation of the region of investigation, and further wherein the shaping of the energy input beam comprises further steps of setting the beam angle of the energy input beam using an aperture comprising a diaphragm or a shutter and adjusting at least one of the diameter of the aperture and the distance between the aperture and the energy input beam source.

2. The method according to claim 1, wherein the groups of parallel energy input beam components provide a complete irradiation of the region of investigation without the energy input beam components belonging to the respective group overlapping.

3. The method according to claim 1, wherein the energy input beam is a fan beam or a cone beam.

4. The method according to claim 1, wherein the step of shaping the energy input beam comprises transmitting the energy input beam through a beam mask made of an energy input shielding material with through holes.

5. The method according to claim 4, wherein the step of shaping the energy input beam comprises transmitting the energy input beam through a plane beam mask with through holes all having an equal size or through a curved beam mask with through holes having different sizes.

6. The method according to claim 4, further comprising the step of adjusting a distance between the beam mask and an energy input beam source.

7. The method according to claim 1, wherein the step of shaping the energy input beam comprises a further step of setting a beam angle ($\alpha$) of the energy input beam.

8. The method according to claim 7, wherein the beam angle ($\alpha$) is set with an aperture.

9. The method according to claim 8, further comprising the step of adjusting at least one of the diameter the aperture and the distance between the aperture and the energy input beam source.

10. The method according to claim 1, wherein the energy input beam components of the energy input beam comprise a distribution of parallel pencil beams.

11. The method according to claim 10, wherein the step of shaping the energy input beam comprises a source modulation for providing the different cross-sections of the parallel pencil beams.

12. The method according to claim 1, wherein the projection directions are set subsequently by moving the energy input beam source relative to the object.

13. The method according to claim 1, wherein a plurality of integrated attenuation values are measured by at least one 1-dimensional linear detector or by at least one 2-dimensional planar detector.

14. The method according to claim 13, wherein the energy input beam components comprise the parallel pencil beams and the integrated attenuation values of all energy input beam components having the same projection direction are simultaneously measured with the detector.

15. The method according to claim 13, wherein exclusively predetermined groups of detector elements of the detector are read out for obtaining the integrated attenuation values.

16. The method according to claim 1, further comprising determining a plurality of projection functions corresponding to the plurality of projection directions, wherein each of the projection functions comprises integrated attenuation values measured with energy input beam components being parallel to the current projection direction and intersecting a reference plane, which is perpendicular to this projection direction at non-equidistant intersection points.

17. The method according to claim 1, further comprising:
subjecting the plurality of integrated attenuation values to a scaling by dividing them by the cross-sections of the respective beam components; and
subjecting the plurality of scaled attenuation values to an image reconstruction procedure.

18. The method according to claim 1, wherein the integrated attenuation values are measured for providing Radon data measured in:
an X-ray computer tomography (CT) device,
light tomography, or
a neutron based transmission detection system.

19. An imaging device for imaging a region of investigation of an object, comprising:
a measuring device for measuring projection functions corresponding to a plurality of projection directions, the measuring device including at least one energy input beam source for creating at least one energy input beam which has a plurality of individual energy input beam components and which has a beam angle describing the divergence of the energy input beam, and a detector device;
a shaping device comprising a beam mask made of an energy input shielding material with through holes each of which is configured to transmit one of the energy input beam components while remaining parts of the energy input beam are shielded, the beam mask being adapted for shaping the energy input beam such that at least two of the energy input beam components being provided for irradiating the region of investigation have different cross-sections and groups of parallel energy input beam components being parallel to one of the projection directions provide a continuous irradiation of the region of investigation;
an aperture comprising a diaphragm or a shutter for setting the beam angle of the energy input beam; and
a second adjustment device for adjusting at least one of the diameter of the aperture and the distance between the aperture and the energy input beam source.

20. The imaging device according to claim 19, wherein the shaping device comprises a beam mask made of an energy input shielding material with through holes.

21. The imaging device according to claim 20, wherein the beam mask is arranged between the at least one energy input beam source and the region of investigation.

22. The imaging device according to claim 20, wherein the shaping device comprises a plane beam mask with through holes all having an equal size or a curved source mask with through holes having different sizes.

23. The imaging device according to claim 20, further comprising a first adjustment device for adjusting a distance between the beam mask and the energy input beam source.

24. The imaging device according to claim 19, wherein the energy input beam source is adapted for creating a fan beam or a cone beam.

25. The imaging device according to claim 19, wherein the detector device comprises at least one 1-dimensional linear detector or at least one 2-dimensional planar detector.

26. The imaging device according to claim 19, wherein the energy input beam source is movable relative to the object.

27. The imaging device according to claim 19, wherein the energy input beam source is adapted for creating parallel pencil beams.

28. The imaging device according to claim 27, wherein the energy input beam source includes a movable radiation emitter and the shaping device comprises a current control for controlling the radiation emitter.

29. The imaging device according to claim 19, further comprising a reconstruction circuit for reconstructing an image function on the basis of measured projection functions.

* * * * *